United States Patent [19]

Avidan et al.

[11] Patent Number: 4,746,762

[45] Date of Patent: May 24, 1988

[54] UPGRADING LIGHT OLEFINS IN A TURBULENT FLUIDIZED CATALYST BED REACTOR

[75] Inventors: Amos A. Avidan, Mantua; Tai-Sheng Chou, Sewell; Hartley Owen, Belle Mead; Jorge L. Soto, Westville; Samuel A. Tabak, Wenonah, all of N.J.

[73] Assignee: Mobil Oil Corporation, New York, N.Y.

[21] Appl. No.: 6,407

[22] Filed: Jan. 23, 1987

Related U.S. Application Data

[60] Continuation-in-part of Ser. No. 824,473, Jan. 31, 1986, Pat. No. 4,689,205, which is a division of Ser. No. 733,994, May 14, 1985, Pat. No. 4,579,999, which is a continuation-in-part of Ser. No. 692,261, Jan. 17, 1985, Pat. No. 4,543,435.

[51] Int. Cl.$^4$ .............................................. C07C 2/12
[52] U.S. Cl. ...................................... 585/415; 585/417; 585/533
[58] Field of Search ......................... 585/415, 533, 417

[56] References Cited

U.S. PATENT DOCUMENTS

| | | | |
|---|---|---|---|
| 3,907,663 | 9/1975 | Owen | 585/415 |
| 4,046,825 | 9/1977 | Owen et al. | 585/415 |
| 4,070,411 | 1/1978 | Butter et al. | 585/700 |
| 4,090,949 | 5/1978 | Owen et al. | 585/415 |
| 4,100,218 | 7/1978 | Chen et al. | 585/310 |
| 4,138,440 | 2/1979 | Chang et al. | 585/640 |
| 4,254,295 | 3/1981 | Tabak | 585/533 |
| 4,283,273 | 8/1981 | Owen | 585/415 |
| 4,417,086 | 11/1983 | Miller | 585/533 |
| 4,417,087 | 11/1983 | Miller | 585/533 |
| 4,517,396 | 5/1985 | Hoek et al. | 585/415 |
| 4,543,435 | 9/1985 | Gould et al. | 585/330 |
| 4,547,616 | 10/1985 | Avidan et al. | 585/640 |
| 4,579,999 | 4/1986 | Gould et al. | 585/312 |
| 4,605,807 | 8/1986 | Mazurek | 585/517 |
| 4,642,403 | 2/1987 | Hyde et al. | 585/415 |
| 4,689,205 | 8/1987 | Gould et al. | 585/312 |

Primary Examiner—Asok Pal
Attorney, Agent, or Firm—Alexander J. McKillop; Michael G. Gilman; L. G. Wise

[57] ABSTRACT

A fluidized bed catalytic process for conversion of light olefinic gas feedstock containing ethene to produce hydrocarbons rich in $C_5^+$ liquids, comprising the steps of maintaining a fluidized bed of zeolite catalyst particles in a turbulent reactor bed at a temperature of about 315° to 510° C., said catalyst having an apparent particle density of about 0.9 to 1.6 g/cm$^3$ and a size range of about 1 to 150 microns, and average catalyst particles size of about 20 to 100 microns containing about 10 to 25 weight percent of fine particles having a particle size less than 32 microns; passing hot feedstock vapor upwardly through the fluidized catalyst bed under turbulent flow conditions; maintaining turbulent fluidized bed conditions through the reactor bed between transition velocity and transport velocity at a superficial fluid velocity of about 0.3 to 2 meters per second; and recovering hydrocarbon product containing a major amount of $C_5^+$ hydrocarbons and containing $C_3$–$C_5$ alkanes and alkenes in the ratio of about 0.2:1 to 5:1.

15 Claims, 5 Drawing Sheets

UPGRADING LIGHT OLEFINS IN A TURBULENT FLUIDIZED CATALYST BED REACTOR

CROSS-REFERENCE TO RELATED APPLICATIONS

This application is a continuation-in-part of U.S. patent application Ser. No. 824,473, filed Jan. 31, 1986, now U.S. Pat. No. 4,689,205, which is a division of U.S. patent application Ser. No. 733,994, filed May 14, 1985, now U.S. Pat. No. 4,579,999, which is a continuation-in-part of U.S. patent application Ser. No. 692,261, filed Jan. 17, 1985, now U.S. Pat. No. 4,543,435.

BACKGROUND OF THE INVENTION

This invention relates to a catalytic technique for upgrading light olefin gas to heavier hydrocarbons. In particular, it provides a continuous process for oligomerizing ethene-containing olefinic light gas feedstock, optionally containing propene or other lower alkenes, to produce $C_4+$ hydrocarbons, such as olefinic liquid fuels, isobutane, aromatics and other useful products. Ethene (ethylene, $C_2H_4$)-containing gases, such as petroleum cracking offgas, are useful feedstocks herein.

Developments in zeolite catalysis and hydrocarbon conversion processes have created interest in utilizing olefinic feedstocks for producing $C_5+$ gasoline, diesel fuel, etc. In addition to basic chemical reactions promoted by ZSM-5 type zeolite catalysts, a number of discoveries have contributed to the development of new industrial processes. These are safe, environmentally acceptable processes for utilizing feedstocks that contain lower olefins, especially $C_2$-$C_4$ alkenes. Conversion of $C_2$-$C_4$ alkenes and alkanes to produce aromatics-rich liquid hydrocarbon products were found by Cattanach (U.S. Pat. No. 3,760,024) and Yan et al (U.S. Pat. No. 3,845,150) to be effective processes using the ZSM-5 type zeolite catalysts. In U.S. Pat. Nos. 3,960,978 and 4,021,502, Plank, Rosinski and Givens disclose conversion of $C_2$-$C_5$ olefins, alone or in admixture with paraffinic components, into higher hydrocarbons over crystalline zeolites having controlled acidity. Garwood et al. have also contributed to the understanding of catalytic olefin upgrading techniques and improved processes as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5+$ aliphatic and aromatic hydrocarbons. Product distribution for liquid hydrocarbons can be varied by controlling process conditions, such as temperature, pressure and space velocity. Gasoline ($C_5$-$C_{10}$) is readily formed at elevated temperature (e.g., up to about 400° C.) and moderate pressure from ambient to about 5500 kPa, preferably about 250 to 2900 kPa. Olefinic gasoline can be produced in good yield and may be recovered as a product or fed to a low severity, high pressure reactor system for furthher conversion to heavier distillate-range products. Distillate mode operation can be employed to maximize production of $C_{10}+$ aliphatics by reacting the lower and intermediate olefins at high pressure and moderate temperature. Operating details for typical "MOGD" oligomerization units are disclosed in U.S. Pat. Nos. 4,456,779; 4,497,968 (Owen et al.) and 4,433,185 (Tabak), incorporated herein by reference. At moderate temperature and relatively high pressure, the conversion conditions favor distillate-range product having a normal boiling point of at least 165° C. (330° F.). Lower olefinic feedstocks containing $C_2$-$C_6$ alkenes may be converted selectively; however, the low severity distillate mode conditions do not convert a major fraction of ethene. While propene, butene-1, and others may be converted to the extent of 50% to 95% in the lower severity moderate temperature distillate mode, only about 10% to 30% of the ethene component will be converted using HZSM-5 or similar acid zeolites. Many feedstocks of commercial interest, such as FCC offgas, dehydrogenation products, ethane cracking by-product, etc., contain both ethene and hydrogen along with $H_2S$ and light aliphatics. Ethene can also be converted at moderate temperature with a bifunctional nickel catalyst.

It has been found that ethene-containing light gas can be upgraded to liquid hydrocarbons rich in olefinic gasoline, isobutane and aromatics by catalytic conversion in a turbulent fluidized bed of solid acid zeolite catalyst under high severity reaction conditions in a single pass or with recycle of gas product. This technique is particularly useful for upgrading FCC light gas, which usually contains significant amounts of ethene, propene, paraffins and hydrogen produced in cracking heavy petroleum oils or the like. By upgrading the by-product light gas, gasoline yield of FCC units can be significantly increased. Accordingly, it is a primary object of the present invention to provide a novel technique for upgrading ethene-containing light gas.

SUMMARY OF THE INVENTION

An improved process has been found for continuous conversion of ethene-containing feedstock to heavier hydrocarbon products wherein the feedstock is contacted at elevated temperature with a fluidized bed of zeolite catalyst under conversion conditions. The improvement comprises maintaining the fluidized catalyst bed in a vertical reactor column having a turbulent reaction zone by passing feedstock gas upwardly through the reaction zone at a velocity greater than dense bed transition velocity in a turbulent regime and less than transport velocity for the average catalyst particle; and withdrawing a portion of coked catalyst from the reaction zone, oxidatively regenerating the withdrawn catalyst and returning regenerated catalyst to the reaction zone at a rate to control catalyst activity and reaction severity. The alkane:alkene ratio in the hydrocarbon product is maintained at about 0.2:1 to 5:1 under conditions of reaction severity to effect feedstock conversion. Advantageously, the fluidized bed technique can employ a single pass ethene conversion of at least 70% to provide high octane gasoline range hydrocarbon product in good yield. A thermmodynamically heat balanced mixture of exothermic alkenes and endothermic alkanes can be converted without significant recycle and/or diluent to provide high octane gasoline range hydrocarbon product in good yield. However, recycle of mostly $C_4-$ gas can be used to increase $C_5+$ yields further and lower catalyst makeup requirements.

THE DRAWINGS

DESCRIPTION OF PREFERRED EMBODIMENTS

Description of Catalysts

Figure 1:
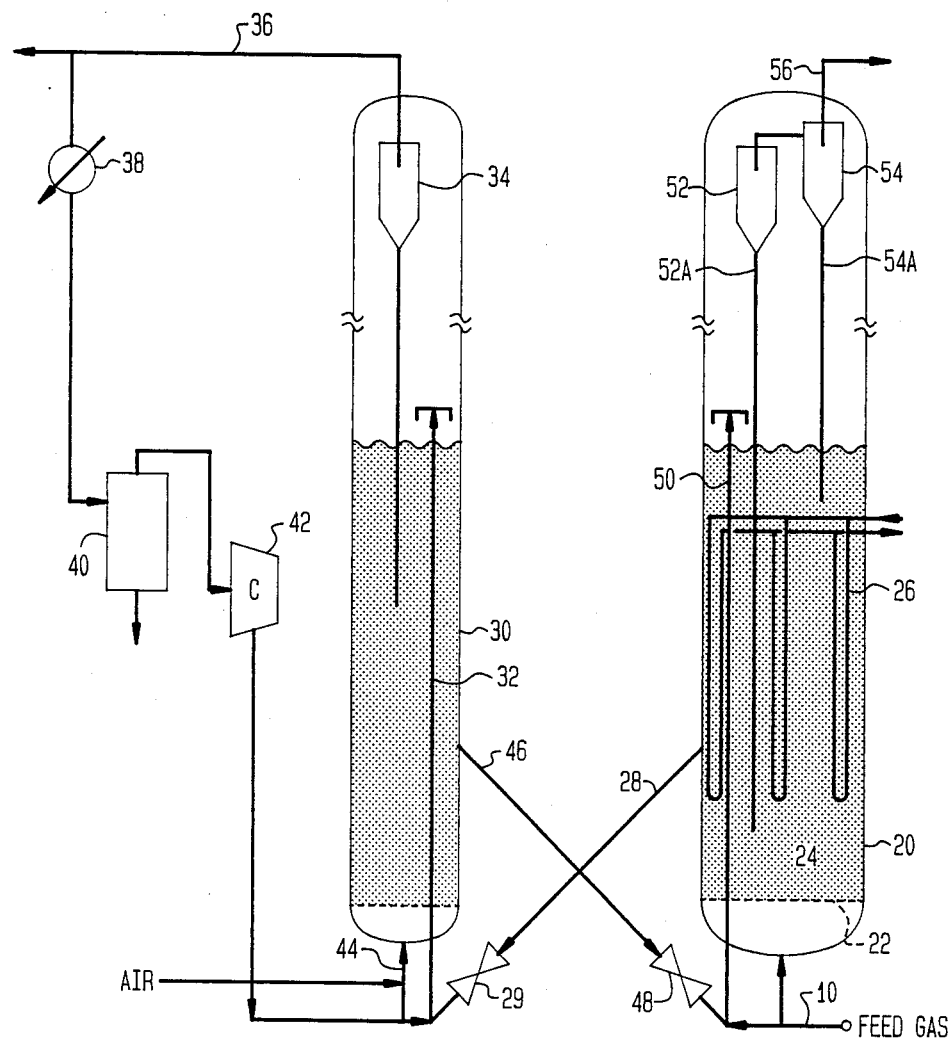
FIG. 1 is a schematic view of a fluidized bed reactor system according to the present invention.

Recent developments in zeolite technology have provided a group of medium pore siliceous materials having similar pore geometry. Most prominent among these intermediate pore size zeolites is ZSM-5, which is usually synthesized with Brönsted acid active sites by incorporating a tetrahedrally coordinated metal, such as Al, Ga, B or Fe, within the zeolitic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization catalysts preferred for use herein include the medium pore (i.e., about 5-7A) shape-selective crystalline aluminosilicate zeolites having a silica-to-alumina ratio of at least 12, a constraint index of about 1 to 12 and acid cracking activity of about 10-250. In the fluidized bed reactor the coked catalyst may have an apparent activity (alpha value) of about 10 to 80 under the process conditions to achieve the required degree of reaction severity. Representative of the ZSM-5 type zeolites are ZSM-5, ZSM-11, ZSM-12, ZSM-22, ZSM-23, ZSM-35 and ZSM-38. ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245 and 4,046,839; 4,414,423; 4,417,086; 4,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Brönsted acid sites may consist essentially of aluminosilicate ZSM-5 zeolite with 5 to 95 wt.% silica and/or alumina binder.

These siliceous zeolites may be employed in their acid forms ion exchanged or impregnated with one or more suitable metals, such as Ga, Pd, Zn, Ni, Co and/or other metals of Periodic Groups III to VIII. The zeolite may include a hydrogenation-dehydrogenation component (sometimes referred to as a hydrogenation component) which is generally one or more metals of group IB, IIB, IIIB, VA, VIA or VIIIA of the Periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as metallic oligomerization component (eg, ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone.

Certain of the ZSM-5 type medium pore shape selective catalysts are sometimes known as pentasils. In addition to the preferred aluminosilicates, the borosilicate, ferrosilicate and "silicalite" materials may be employed. It is advantageous to employ a standard ZSM-5 having a silica:alumina molar ratio of 25:1 to 70:1 with an apparent alpha value of 10–80 to convert 60 to 100 percent, preferably at least 70%, of the olefins in the feedstock.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred. In order to obtain the desired particle size for fluidization in the turbulent regime, the zeolite catalyst crystals are bound with a suitable inorganic oxide, such as silica, alumina, etc. to provide a zeolite concentration of about 5 to 95 wt. %. In the description of preferred embodiments a 25% H-ZSM-5 catalyst contained within a silica-alumina matrix and having a fresh alpha value of about 80 is employed unless otherwise stated.

Particle size distribution can be a significant factor in achieving overall homogeneity in turbulent regime fluidization. It is desired to operate the process with particles that will mix well throughout the bed. Large particles havin a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. This class of fluidizable particles is classified as Geldart Group A. Accordingly, the fluidization regime is controlled to assure operation between the transition velocity and transport velocity. Fluidization conditions are substantially different from those found in non-turbulent dense beds or transport beds.

Process Operation

In this description, metric units and parts by weight are employed unless otherwise stated.

The preferred feedstock contains $C_2$-$C_6$ alkenes (mono-olefin) including at least 2 mole % ethene, wherein the total $C_2$-$C_3$ alkenes are in the range of about 10 to 40 wt%. Non-deleterious components, such as methane and other paraffins and inert gases, may be present. A particularly useful feedstock is a light gas by-product of FCC gas oil cracking units containing typically 10–40 mol % $C_2$-$C_4$ olefins and 5–35 mol % $H_2$ with varying amounts of $C_1$-$C_3$ paraffins and inert gas, such as $N_2$. The process may be tolerant of a wide range of lower alkanes, from 0 to 95%. Preferred feedstocks contain more than 50 wt. % $C_1$-$C_4$ lower aliphatic hydrocarbons, and contain sufficient olefins to provide total olefinic partial pressure of at least 50 kPa.

Under the severity reaction conditions employed in the present invention, propane, if present, may be partially converted to $C_4^+$ products.

The desired products are $C_4$ to $C_9$ hydrocarbons, which will comprise at least 50 wt.% of the recovered product, preferably 80% or more. While olefins may be a predominant fraction of the $C_4^+$ reaction effluent, up to 45% butenes, pentenes, hexenes, heptenes, octenes, nonenes and their isomers; it is desired to upgrade the feedstock to high octane gasoline containing aromatics, preferably at least 10% by weight.

The reaction severity conditions can be controlled to optimize yield of $C_4$-$C_9$ aliphatic hydrocarbons. It is understood that aromatics and light paraffin production is promoted by those zeolite catalysts having a high concentration of Bronsted acid reaction sites. Accordingly, an important criterion is selecting and maintaining catalyst inventory to provide either fresh catalyst having acid activity or by controlling catalyst deactivation and regeneration rates to provide an apparent average alpha value of about 10 to 80.

Figure 6:
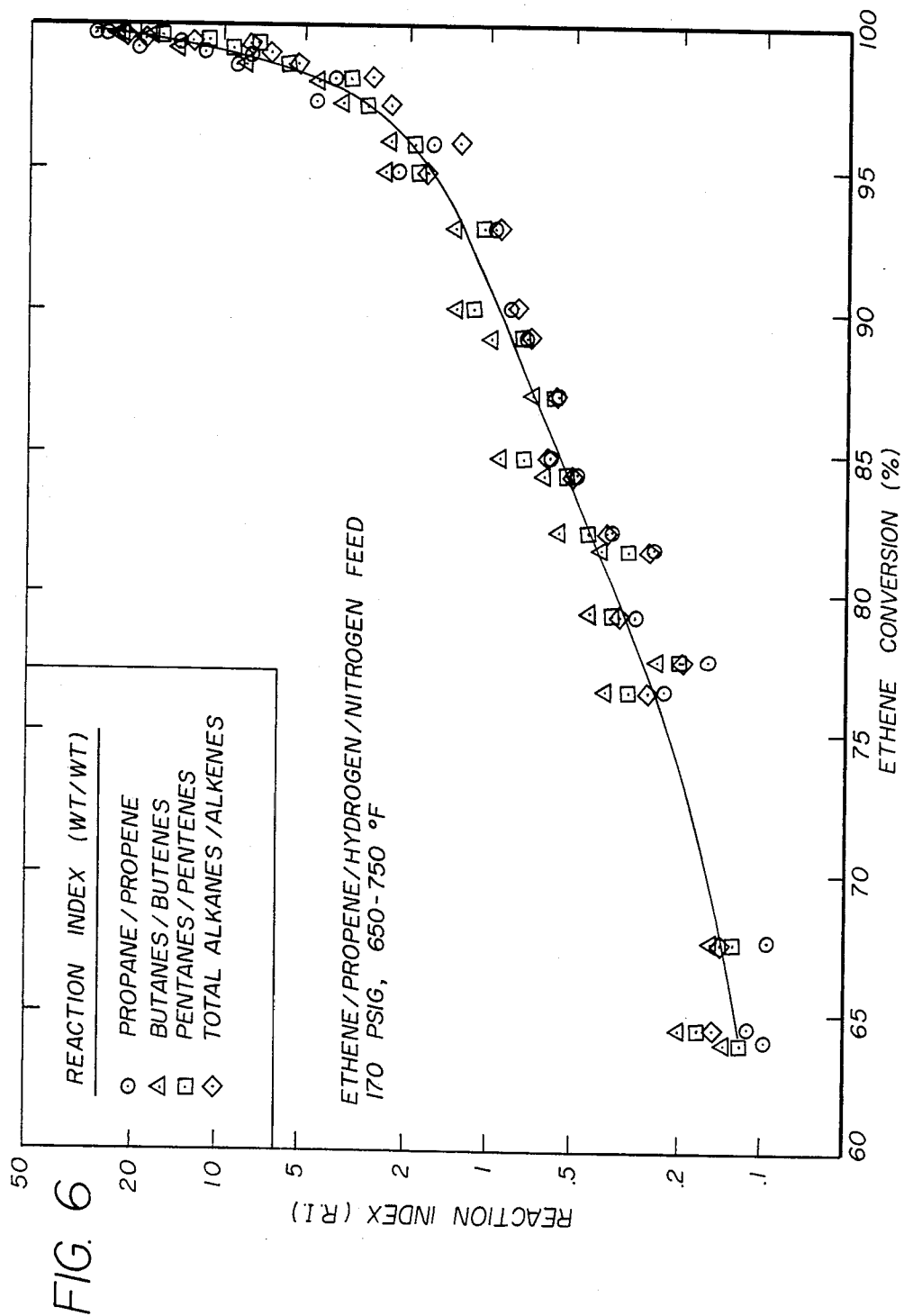
FIG. 6 is a semilog plot comparing $C_3$-$C_5$ alkane:alkene.

Reaction temperatures and contact time are also significant factors in the reaction severity, and the process parameters are followed to give a substantially steady state condition wherein the reaction severity index (R.I.) is maintained to yield a desired weight ratio of propane to propene. Though it appears this index may vary from about 0.1 to 200 in the presence of added propane, it is preferred to operate the steady state fluidized bed unit to hold the R.I. at about 0.2:1 to 5:1, in the substantial absence of added propane. While reaction severity is advantageously expressed as the weight ratio of propane:propene in the gaseous phase, it may also be approximated by the analogous ratios of butanes:butenes, pentanes:pentenes, or the average of total reactor effluent alkanes:alkenes in the $C_3$-$C_5$ range. FIG. 6 shows the close relationship between R.I. value for $C_3$, $C_4$ and $C_5$ aliphatics and total alkane:alkene ratio. These values are shown in the range of 0.1 to 50 with typical $C_2$-$C_3$ olefinic feedstock in the substantial absence of added propane in the feedstock. The optimum value will depend upon the exact catalyst composition, feedstock and reaction conditions; however, the typical ethene-containing light gas mixtures used in the examples herein and similar cracking process off-gas can be optionally upgraded to the desired aliphatic-rich gasoline by keeping the R.I. at about 1.

The olefinic feedstream may be enriched by addition of propane to increase the production of $C_4^+$ product. Propane containing streams, such as $C_3$-$C_4$ LPG and various refinery fractiins can be employed to supplement the olefinic feedstock. Suitable $C_2$-$C_4$ aliphatic mixtures containing 20 to 85 wt. % propane may enhance olefinic feedstocks of 15 to 79% mono-alkene. Since propane conversion is incomplete under ordinary operating conditions, this addition can raise the apparent $C_3$ R.I. value above 50:1.

Upgrading of olefins by such hydrogen contributors in fluidized bed cracking and oligomerization units is taught by Owen et al in U.S. Pat. No. 4,090,949. This technique is particularly useful for operation with a fluidized catalytic cracking (FCC) unit to increase overall production of liquid product in fuel gas limited petroleum refineries. Light olefins and some of the light paraffins, such as those in FCC fuel gas, can be converted to valuable $C_4^+$ hydrocarbon product in a fluidbed reactor containing a zeolite catalyst. In addition to fuel gas upgrading, the load to the refinery fuel gas plant is decreased considerably. This allows operation of the FCC unit at higher throughput and/or higher severity in fuel gas limited refineries.

The use of fluidized bed catalysis permits the conversion system to be operated at low pressure drop, which in an economically practical operation can provide a maximum operating pressure only 50 to 200 kPa above atmospheric pressure. Another important advantage is the close temperature control that is made possible by turbulent regime operation, wherein the uniformity of conversion temperature can be maintained within close tolerances, often less than 25° C. Except for a small zone adjacent the bottom gas inlet, the midpoint measurement is representative of the entire bed, due to the thorough mixing achieved.

In a typical process, the ethene-containing $C_2^+$ olefinic feedstock is converted in a catalytic reactor under oligomerization conditions and moderate pressure (ie- 410 to 2500 kPa) to produce at least 6% isobutane and a predominantly liquid product consisting essentially of $C_4^+$ hydrocarbons rich in gasoline-range olefins and aromatics.

Referring now to FIG. 1, feed gas rich in $C_2$-$C_3$ olefins passes under pressure through conduit 10, with the main flow being directed through the bottom inlet of reactor vessel 20 for distribution through grid plate 22 into the fluidization zone 24. Here the feed gas contacts the turbulent bed of finely divided catalyst particles. Reactor vessel 2 is shown provided with heat exchange tubes 26, which may be arranged as several separate heat exchange tube bundles so that temperature control can be separately exercised over different portions of the fluid catalyst bed. The bottoms of the tubes are spaced above feed distributor grid 22 sufficiently to be free of jet action by the charged feed through the small diameter holes in the grid. Alternatively, reaction heat can be partially or completely removed by using cold feed. Baffles may be added to control radial and axial mixing. Although depicted without baffles, the vertical reaction zone can contain open end tubes above the grid for maintaining hydraulic constraints, as disclosed in U.S. Pat. No. 4,251,484 (Daviduk and Haddad). Heat released from the reaction can be controlled by adjusting feed temperature in a known manner.

Catalyst outlet means 28 is provided for withdrawing catalyst from above bed 24 and passed for catalyst regeneration in vessel 30 via control valve 29. The partially deactivated catalyst is oxidatively regenerated by controlled contact with air or other regeneration gas at elevated temperature in a fluidized regeneration zone to remove carbonaceous deposits and restore acid activity. The catalyst particles are entrained in a lift gas and transported via riser tube 32 to a top portion of vessel 30. Air is distributed at the bottom of the bed to effect fluidization, with oxidation byproducts being carried out of the regeneration zone through cyclone separator 34, which returns any entrained solids to the bed. Flue gas is withdrawn via top conduit 36 for disposal; however, a portion of the flue gas may be recirculated via heat exchanger 38, separator 40, and compressor 42 for return to the vessel with fresh oxidation gas via line 44 and as lift gas for the catalyst in riser 32.

Regenerated catalyst is passed to the main reactor 20 through conduit 46 provided with flow control valve 48. The regenerated catalyst may be lifted to the catalyst bed with pressurized feed gas through catalyst return riser conduit 50. Since the amount of regenerated catalysts passed to the reactor is ralatively small, the temperature of the regenerated catalyst does not upset the temperature constraints of the reactor operations in significant amount. A series of sequentially connected cyclone separators 52, 54 are provided with diplegs 52A, 54A to return any entrained catalyst fines to the lower bed. These separators are positioned in an upper portion of the reactor vessel comprising dispersed catalyst phase 24. Filters, such as sintered metal plate filters, can be used alone or in conjunction with cyclones.

The product effluent separated from catalyst particles in the cyclone separating system is then withdrawn from the reactor vessel 20 through top gas outlet means 56. The recovered hydrocarbon product comprising $C_5+$ olefins and/or aromatics, paraffins and naphthenes is thereafter processed as required to provide a desired gasoline or higher boiling product.

Under optimized process conditions the turbulent bed has a superficial vapor velocity of about 0.3 to 2 meters per second (m/sec). At higher velocities entrainment of fine particles may become excessive and beyond about 3 m/sec the entire bed may be transported out of the reaction zone. At lower velocities, the formation of large bubbles or gas voids can be detrimental to conversion. Even fine particles cannot be maintained effectively in a turbulent bed below about 0.1 m/sec.

A convenient measure of turbulent fluidization is the bed density. A typical turbulent bed has an operating density of about 100 to 500 kg/m$^3$, preferably about 300 to 500 kg/m$^3$, measured at the bottom of the reaction zone, becoming less dense toward the top of the reaction zone, due to pressure drop and particle size differentiation. Pressure differential between two vertically spaced points in the reactor column can be measured to obtain the average bed density at such portion of the reaction zone. For instance, in a fluidized bed system employing ZSM-5 particles having an apparent packed density of 750 kg/m$^3$ and real density of 2430 kg/m$^3$, an average fluidized bed density of about 300 to 500 kg/m$^3$ is satisfactory.

By virtue of the turbulence experienced in the turbulent regime, gas-solid contact in the catalytic reactor is improved, providing at least 70% ethene conversion, enhanced selectivity and temperature uniformity. One main advantage of this technique is the inherent control of bubble size and characteristic bubble lifetime. Bubbles of the gaseous reaction mixture are small, random and short-lived, thus resulting in good contact between the gaseous reactants and the solid catalyst particles.

A significant difference between the process of this invention and conversion processes of the prior art is that operation in the turbulent fluidization regimeis optimized to produce high octane $C_5+$ liquid in good yield. The weight hourly space velocity and uniform contact provides a close control of contact time between vapor and solid phases, typically about 3 to 15 seconds. Another advantage of operating in such a mode is the control of bubble size and life span, thus avoiding large scale gas by-passing in the reactor.

As the superficial gas velocity is increased in the dense bed, eventually slugging conditions occur and with a further increase in the superficial gas velocity the slug flow breaks down into a turbulent regime. The transition velocity at which this turbulent regime occurs appears to decrease with particle size. The turbulent regime extends from the transition velocity to the so-called transport velocity, as described by Avidan et al in U.S. Pat. No. 4,547,616, incorporated herein by reference. As the transparent velocity is approached, there is a sharp increase in the rate of particle carryover, and in the absence of solid recycle, the bed could empty quickly.

Several useful parameters contribute to fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range from 0.6–2 g/cc, preferably 0.9–1.6 g/cc. The catalyst particles can be in a wide range of particle sizes up to about 250 microns, with an average particle size between about 20 and 100 microns, preferably in the range of 10–150 microns and with the average particle size between 40 and 80 microns. When these solid particles are placed in a fluidized bed where the superficial fluid velocity is 0.3–2 m/s, operation in the turbulent regime is obtained. Those skilled in the art will appreciate that at higher pressures, a lower gas velocity may be employed to ensure operation in the turbulent fluidization regime.

The reactor can assume any technically feasible configuration, but several important criteria should be considered. The bed of catalyst in the reactor can be at least about 5–20 meters in height, preferably about 9 meters. Fine particles may be included in the bed, especially due to attrition, and the fines may be entrained in the product gas stream. A typical turbulent bed may have a catalyst carryover rate up to about 1.5 times the reaction zone inventory per hour. If the fraction of fines becomes large, a portion of the carryover can be removed from the system and replaced by larger particles. It is feasible to have a fine particle separator, such as a cyclone and/or filter means, disposed within or outside the reactor shell to recover catalyst carryover and return this fraction continuously to the bottom of the reaction zone for recirculation at a rate of about one catalyst inventory per hour. Optionally, fine particles carried from the reactor vessel entrained with effluent gas can be recovered by a high operating temperature sintered metal filter.

This process can be used with any process stream which contains sufficient light olefins and paraffins. For example, it can be used to process FCC by-product fuel gas, which typically contains about 10 to 40 wt. % total ethene and propene. Experimental runs are performed using a ZSM-5 catalyst to demonstrate the inventive process. The fluidized bed unit can be operated over a wide range of process variables and catalyst activity.

Reactor Operation

A typical reactor unit employs a temperature-controlled catalyst zone with indirect heat exchange and/or adjustable gas quench, whereby the reaction exotherm can be carefully controlled to prevent excessive temperature above the usual operating range of about 315° C. to 510° C., preferably at average reactor temperature of 315° C. to 430° C. Energy conservation in the system may utilize at least a portion of the reactor exotherm heat value by exchanging hot reactor effluent with feedstock and/or recycle streams. Optional heat exchangers may recover heat from the effluent stream prior to fractionation. Part of all of the reaction heat can be removed from the reactor without using the indirect heat exchange tubes by using cold feed, whereby reactor temperature can be controlled by adjusting feed temperature. The internal heat exchange tubes can still be used as internal baffles which lower reactor hydraulic diameter, and axial and radial mixing.

The weight hourly space velocity (WHSV, based on total olefins in the fresh feedstock is about 0.1-5 WHSV. Typical product fractionation systems are described in U.S. Pat. Nos. 4,456,779 and 4,504,693 (Owen, et al.). Typical results, obtained in a fluid bed reactor, are shown in Examples 1-3.

EXAMPLE 1

| Reactor Conditions: | |
| --- | --- |
| Temperature | 370° C. |
| Pressure | 410 kPa |
| Olefin-WHSV | 0.5 |
| No Recycle | |
| Feed Composition, wt. % | |
| Hydrogen | 10.7 |
| Ethene | 89.3 |
| Product Yields | |
| Methane | 0.1 |
| Ethane | 1.9 |
| Ethene | 11.7 |
| Propane | 7.3 |
| Propene | 5.0 |
| Isobutane | 10.6 |
| n-Butane | 4.4 |
| Butenes | 7.6 |
| $C_5^+$ Hydrocarbons | 51.4 |
| $C_5^+$ Hydrocarbon Properties | |
| R + O Octane | 93.2 |
| Specific Gravity | 0.74 |

EXAMPLE 2

| Reactor Conditions: | |
| --- | --- |
| Temperature | 370° C. |
| Pressure | 1200 kPa |
| Olefin-WHSV | 0.4 |
| No Recycle | |
| Feed Composition, wt. % | |
| Nitrogen | 65.8 |
| Hydrogen | 0.8 |
| Ethene | 14.7 |
| Propene | 18.7 |
| Product Yields | |
| Methane | 0.1 |
| Ethane | 1.4 |
| Ethene | 3.6 |
| Propane | 8.9 |
| Propene | 2.8 |
| Isobutane | 12.8 |
| n-Butane | 6.0 |
| Butenes | 5.7 |
| $C_5^+$ Hydrocarbons | 58.7 |
| $C_5^+$ Hydrocarbon Properties | |
| R + O Octane | 93.2 |
| Specific Gravity | 0.74 |

EXAMPLE 3

| Reactor Conditions: | |
| --- | --- |
| Temperature | 370° C. |
| Pressure | 1200 kPa |
| Olefin-WHSV | 0.4 |
| Recycle ratio, Mol/Mole | 1.4 |
| Feed Composition, wt. % | |
| Nitrogen | 65.8 |
| Hydrogen | 0.8 |
| Ethene | 14.7 |
| Propene | 18.7 |
| Product Yields | |

| -continued | |
| --- | --- |
| Methane | 0.1 |
| Ethane | 0.7 |
| Ethene | 6.0 |
| Propane | 4.7 |
| Propene | 3.0 |
| Isobutane | 9.9 |
| n-Butane | 3.6 |
| Butenes | 6.3 |
| $C_5^+$ Hydrocarbons | 65.7 |
| $C_5^+$ Hydrocarbon Properties | |
| R + O Octane | 90.3 |
| Specific Gravity | 0.73 |

Example 1 is for a feed containing only ethene and hydrogen. Example 2 is for a feed containing nitrogen, hydrogen, ethene and propene. Example 3 is similar to Example 2, but a substantial portion of the $C_4^-$ product is recycled back to the reactor. $C_5^+$ yields are higher and catalyst makeup requirements are lower for Example 3 compared to Example 2.

Higher isobutane yields, and higher gasoline octane numbers are possible at higher temperatures, lower pressures, and higher catalyst activity. This is illustrated in Example 4 and graphic plots in FIGS. 2, 3, 4 and 5.

Figure 2:
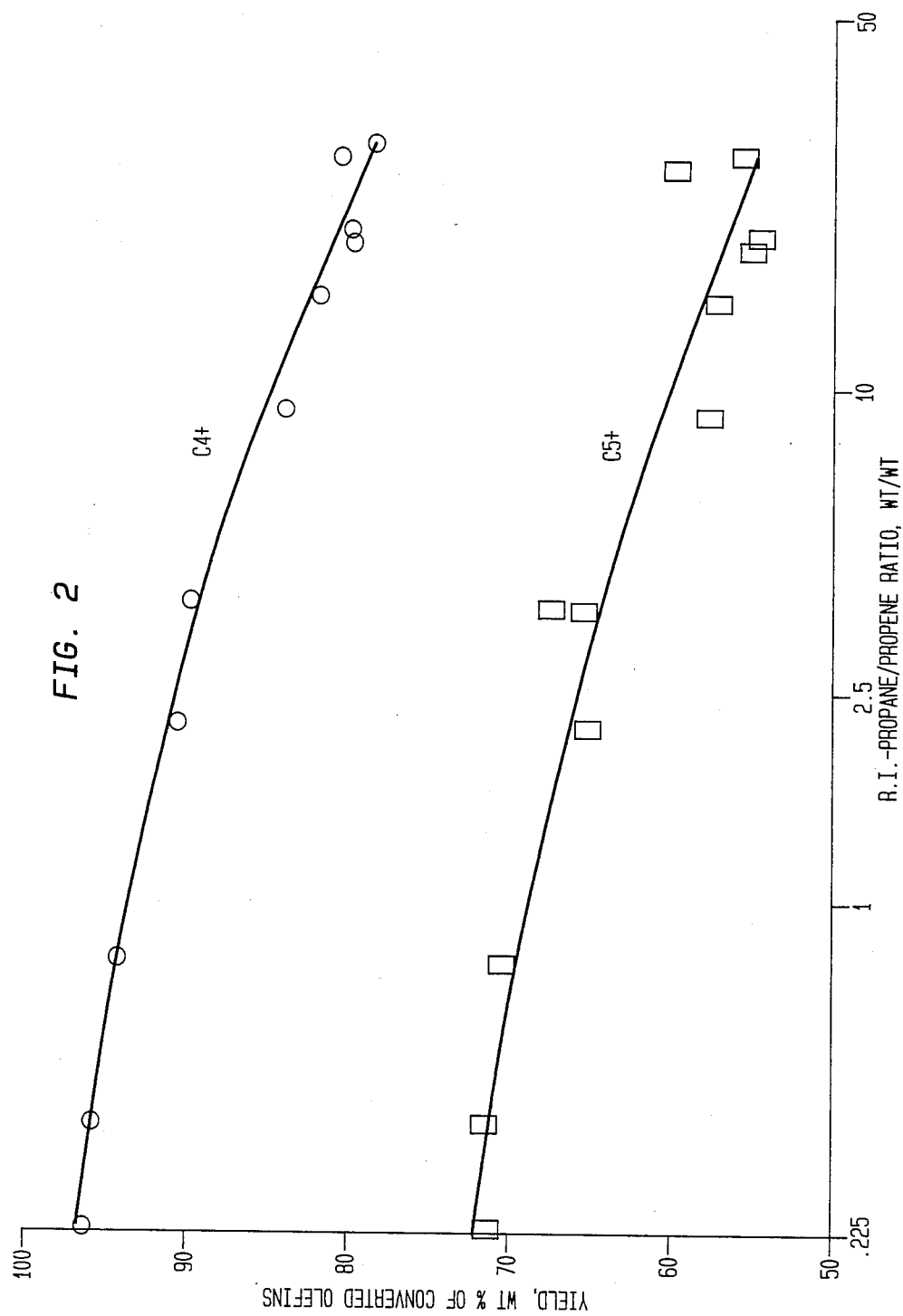
FIG. 2 is a graphic plot showing product yields vs. reaction severity index (R.I.)
Figure 3:
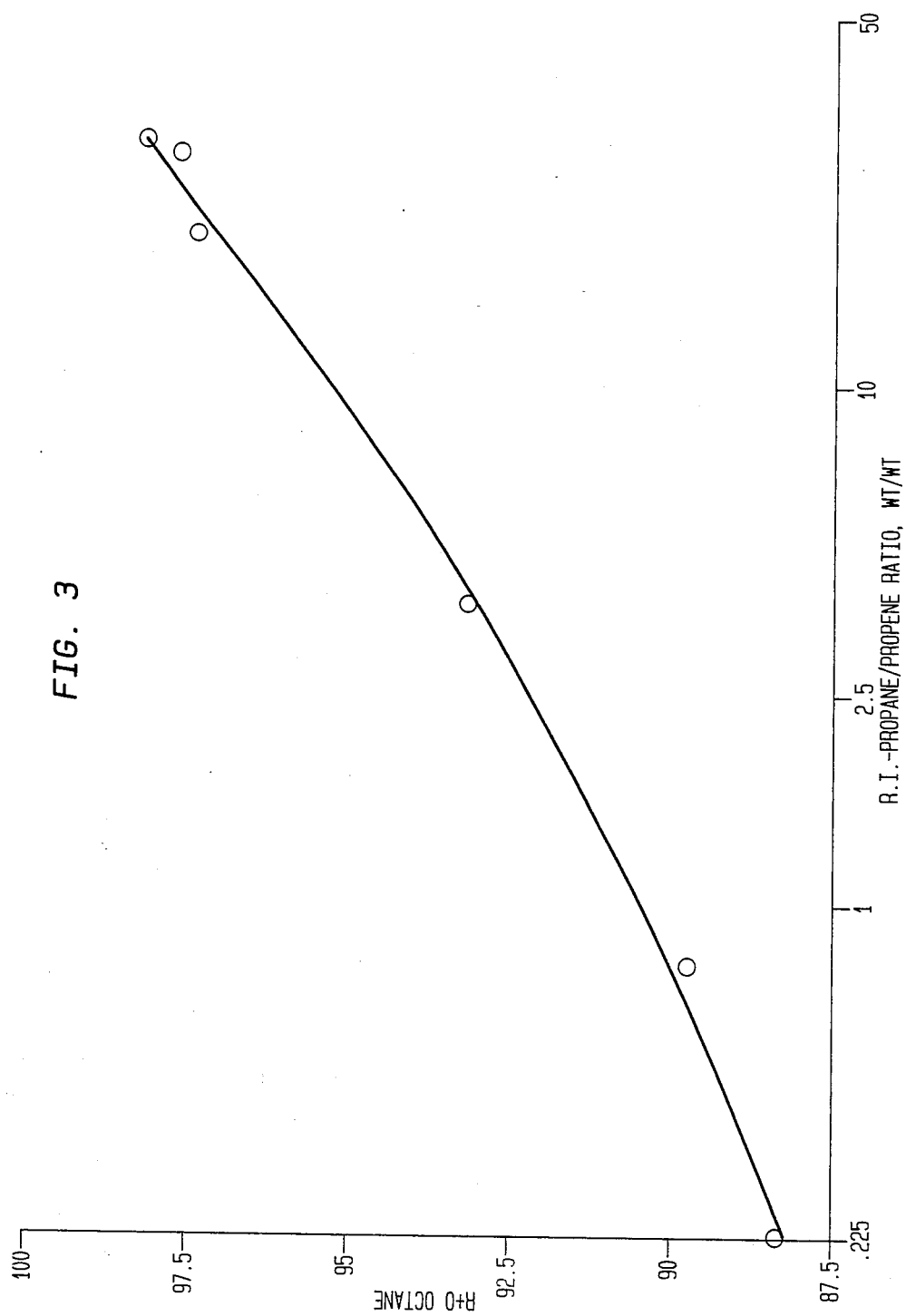
FIG. 3 shows corresponding liquid product octane vs R.I.
Figure 4:
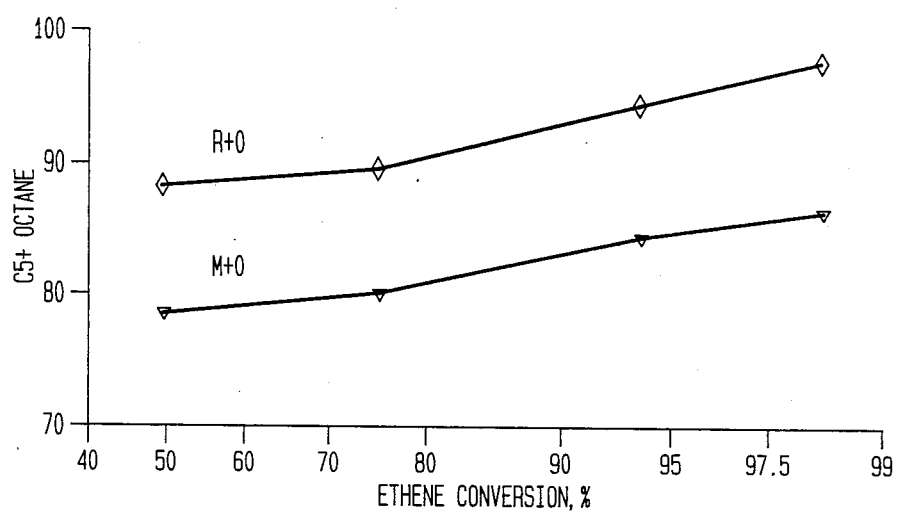
FIG. 4 shows corresponding research and motor octane numbers.
Figure 5:
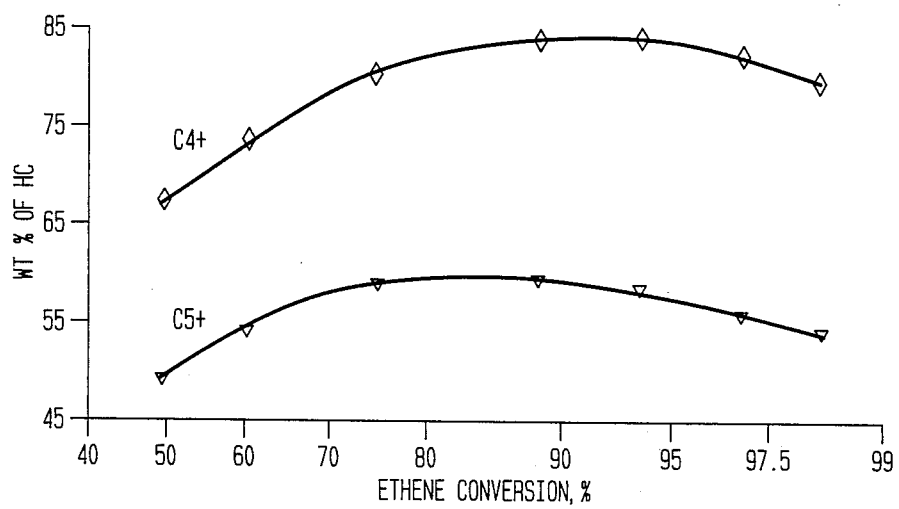
FIG. 5 shows product yield vs ethane conversion.

$C_4^+$ and $C_5^+$ yields, and the respective $C_5^+$ fraction octane number are plotted vs the reaction severity index (propane to propene ratio) in FIGS. 2 and 3. Yields and research and motor octane numbers are plotted vs ethene conversion in FIGS. 4 and 5. Either ethene conversion or the reaction index can be used to characterize reaction severity.

The produced isobutane, usually more than 10 wt. %, may have significant impact on potential alkylate yield, depending on the supply situation of isobutane in a petroleum refinery. The maximum yield ($C_5^+$ plus alkylates) may be achieved at a conversion temperature between 360° to 415° C. The flexibility of the fluid bed for controlling the reactor temperature under exothermic reaction conditions allows an easy adjustment for achieving the optimal yield structure. The proposed fuel gas conversion unit can fit into an existing FCC gas plant, with appropriate amine scrubbing to remove most of the deleterious sulfur compounds, such as $H_2S$.

EXAMPLE 4

| Reactor Conditions: | | | | |
| --- | --- | --- | --- | --- |
| Pressure, psig | 410 kPa | | | |
| Olefin-WHSV | 0.4 | | | |
| Feed Composition, wt. % | | | | |
| Hydrogen | 10.7 | | | |
| Ethene | 89.3 | | | |
| Reactor temperature, °C. | 340 | 370 | 400 | 425 |
| Ethene Conversion, wt. % | 70.8 | 88.4 | 96.5 | 96.8 |
| Yield, wt. % | | | | |
| Propene | 5.0 | 4.8 | 3.6 | 3.9 |
| Butene | 9.5 | 7.4 | 4.1 | 3.8 |
| Isobutane | 5.9 | 11.4 | 15.3 | 14.4 |
| $C_5^+$ HC | 43.1 | 50.9 | 48.1 | 42.9 |
| $C_5^+$ HC R + O Octane | 89.0 | 93.4 | 96.8 | 98.3 |
| $C_5^+$ plus maximum potential alkylate refinery with | | | | |
| excess iC4 | 74.3 | 77.4 | 65.0 | 59.9 |
| iC4 short | 54.7 | 73.3 | 78.2 | 71.2 |

The use of a fluid-bed reactor in this process offers several advantages over a fixed-bed reactor. Due to continuous catalyst regeneration, fluid-bed reactor operation will not be adversely affected by oxygenate, sulfur and/or nitrogen containing contaminants pres-